United States Patent
Thramann

(10) Patent No.: US 8,740,941 B2
(45) Date of Patent: Jun. 3, 2014

(54) PEDICLE BASED SPINAL STABILIZATION WITH ADJACENT VERTEBRAL BODY SUPPORT

(75) Inventor: Jeffery Thramann, Longmont, CO (US)

(73) Assignee: Lanx, Inc., Broomfield, CO (US)

( * ) Notice: Subject to any disclaimer, the term of this patent is extended or adjusted under 35 U.S.C. 154(b) by 909 days.

(21) Appl. No.: 11/938,687

(22) Filed: Nov. 12, 2007

(65) Prior Publication Data

US 2008/0208256 A1 Aug. 28, 2008

Related U.S. Application Data

(60) Provisional application No. 60/865,359, filed on Nov. 10, 2006.

(51) Int. Cl.
*A61B 17/70* (2006.01)

(52) U.S. Cl.
USPC ........... 606/246; 606/248; 606/249; 606/250; 606/278

(58) Field of Classification Search
USPC ............... 606/246–279, 60; 623/17.11–17.16
See application file for complete search history.

(56) References Cited

U.S. PATENT DOCUMENTS

| | | |
|---|---|---|
| 4,599,085 A | 7/1986 | Riess et al. |
| 4,653,481 A | 3/1987 | Howland et al. |
| 5,005,562 A | 4/1991 | Cotrel |
| 5,074,864 A | 12/1991 | Cozad et al. |
| 5,147,359 A | 9/1992 | Cozad et al. |
| 5,154,718 A | 10/1992 | Cozad et al. |
| 5,180,393 A | 1/1993 | Commarmond |
| 5,201,734 A | 4/1993 | Cozad et al. |
| 5,306,275 A | 4/1994 | Bryan |
| 5,366,455 A * | 11/1994 | Dove et al. ................ 606/250 |
| 5,470,333 A | 11/1995 | Ray |
| 5,496,318 A | 3/1996 | Howland et al. |
| 5,531,745 A | 7/1996 | Ray |
| 5,609,634 A | 3/1997 | Voydeville |
| 5,645,599 A | 7/1997 | Samani |
| 5,658,335 A | 8/1997 | Allen |
| 5,683,390 A | 11/1997 | Metz-Stavenhagen et al. |
| 5,683,404 A | 11/1997 | Johnson |
| 5,702,452 A * | 12/1997 | Argenson et al. ........... 606/253 |
| 5,725,582 A | 3/1998 | Bevan et al. |
| 5,800,550 A | 9/1998 | Sertich |
| 5,810,815 A * | 9/1998 | Morales ..................... 606/250 |

(Continued)

FOREIGN PATENT DOCUMENTS

| | | | | |
|---|---|---|---|---|
| EP | 1138268 A1 * | 10/2001 | ............ | A61B 17/70 |
| FR | 2799948 A1 * | 4/2001 | ............ | A61B 17/70 |

(Continued)

OTHER PUBLICATIONS

Translation of WO 2006/106268.*

(Continued)

*Primary Examiner* — Jerry Cumberledge
(74) *Attorney, Agent, or Firm* — Perkins Coie LLP

(57) ABSTRACT

A fastener and rod fusion device with extensions to support an adjacent vertebral body is provided. The extensions are connected to the fastener and rod fusion device. The extensions include flexibly connected rods, bands, spacers, or the like to resist extension and/or flexion of the vertebral body (ies) adjacent a fusion site. Alternatively, the extensions may be coupled to a cross link between multiple rods.

10 Claims, 9 Drawing Sheets

(56) References Cited

U.S. PATENT DOCUMENTS

| | | | |
|---|---|---|---|
| 5,836,948 | A | 11/1998 | Zucherman et al. |
| 5,928,232 | A * | 7/1999 | Howland et al. ............... 606/276 |
| 6,113,602 | A | 9/2000 | Sand |
| 6,135,772 | A | 10/2000 | Jones |
| 6,156,040 | A | 12/2000 | Yonemura et al. |
| 6,277,094 | B1 | 8/2001 | Schendel |
| 6,293,949 | B1 | 9/2001 | Justis et al. |
| 6,440,169 | B1 | 8/2002 | Elberg et al. |
| 6,451,019 | B1 | 9/2002 | Zucherman et al. |
| 6,548,569 | B1 | 4/2003 | Williams et al. |
| 6,582,433 | B2 | 6/2003 | Yun |
| 6,599,294 | B2 | 7/2003 | Fuss et al. |
| 6,626,909 | B2 * | 9/2003 | Chin ............................ 606/276 |
| 6,626,944 | B1 * | 9/2003 | Taylor ........................ 623/17.16 |
| 6,635,060 | B2 | 10/2003 | Hanson et al. |
| 6,641,582 | B1 | 11/2003 | Hanson et al. |
| 6,652,527 | B2 | 11/2003 | Zucherman et al. |
| 6,719,795 | B1 | 4/2004 | Cornwall et al. |
| 6,761,720 | B1 * | 7/2004 | Senegas ........................ 606/249 |
| 6,783,527 | B2 | 8/2004 | Drewry et al. |
| 6,800,084 | B2 | 10/2004 | Davison et al. |
| 6,824,565 | B2 | 11/2004 | Muhanna et al. |
| 6,838,493 | B2 | 1/2005 | Williams et al. |
| 6,946,000 | B2 * | 9/2005 | Senegas et al. ............ 623/17.11 |
| 7,018,379 | B2 | 3/2006 | Drewry et al. |
| 7,029,475 | B2 | 4/2006 | Panjabi |
| 8,092,497 | B2 * | 1/2012 | Pasquet et al. ................ 606/248 |
| 2001/0012938 | A1 | 8/2001 | Zucherman et al. |
| 2002/0029039 | A1 | 3/2002 | Zucherman et al. |
| 2002/0040222 | A1 * | 4/2002 | Hashimoto et al. ............. 606/61 |
| 2002/0040223 | A1 * | 4/2002 | Sato et al. ........................ 606/61 |
| 2002/0147449 | A1 | 10/2002 | Yun |
| 2002/0156150 | A1 | 10/2002 | Williams et al. |
| 2002/0173558 | A1 | 11/2002 | Williams et al. |
| 2003/0153915 | A1 * | 8/2003 | Nekozuka et al. ............... 606/61 |
| 2003/0180266 | A1 | 9/2003 | McKay et al. |
| 2003/0187509 | A1 | 10/2003 | LeMole, Jr. |
| 2003/0216736 | A1 | 11/2003 | Robinson et al. |
| 2003/0225021 | A1 | 12/2003 | McKay et al. |
| 2004/0024458 | A1 | 2/2004 | Senegas et al. |
| 2004/0049188 | A1 * | 3/2004 | Slivka et al. .................... 606/61 |
| 2004/0059337 | A1 | 3/2004 | Hanson et al. |
| 2004/0059339 | A1 | 3/2004 | Roehm, III et al. |
| 2004/0106995 | A1 | 6/2004 | Le Couedic et al. |
| 2004/0158245 | A1 * | 8/2004 | Chin ................................ 606/61 |
| 2004/0167520 | A1 | 8/2004 | Zucherman et al. |
| 2004/0199168 | A1 | 10/2004 | Bertagnoli et al. |
| 2005/0033434 | A1 * | 2/2005 | Berry ........................ 623/17.14 |
| 2005/0085812 | A1 | 4/2005 | Sherman et al. |
| 2005/0101953 | A1 * | 5/2005 | Simonson ........................ 606/61 |
| 2005/0131409 | A1 * | 6/2005 | Chervitz et al. ................. 606/61 |
| 2005/0143737 | A1 | 6/2005 | Pafford et al. |
| 2005/0228381 | A1 * | 10/2005 | Kirschman ..................... 606/61 |
| 2005/0245929 | A1 * | 11/2005 | Winslow et al. ................ 606/61 |
| 2005/0267579 | A1 * | 12/2005 | Reiley et al. ............... 623/17.11 |
| 2006/0015181 | A1 * | 1/2006 | Elberg ........................ 623/16.11 |
| 2006/0084991 | A1 * | 4/2006 | Borgstrom et al. .............. 606/61 |
| 2006/0241601 | A1 * | 10/2006 | Trautwein et al. .............. 606/61 |
| 2006/0247625 | A1 * | 11/2006 | Morrison et al. ................ 606/61 |
| 2006/0271055 | A1 | 11/2006 | Thramann |
| 2007/0093816 | A1 * | 4/2007 | Arnin et al. ..................... 606/61 |
| 2007/0162000 | A1 * | 7/2007 | Perkins ........................... 606/61 |
| 2009/0036925 | A1 * | 2/2009 | Sala et al. ...................... 606/246 |
| 2011/0106163 | A1 * | 5/2011 | Hochschuler et al. ........ 606/264 |

FOREIGN PATENT DOCUMENTS

| | | | |
|---|---|---|---|
| FR | WO2006/106268 | * | 10/2006 |
| WO | WO 2004/073533 A1 | | 8/2004 |
| WO | WO 2006106268 | * | 10/2006 |
| WO | WO 2006106268 A2 | * | 10/2006 |

OTHER PUBLICATIONS

Pasquet, Denis; WO 2006106268 A2; Oct. 2006; Property Organization (WIPO), machine translation.*

Search Report issued May 13, 2008 for Application No. PCT/US2007/081542.

International Bureau Notification Concerning Transmittal of International Preliminary Report on Patentability (Chapter I of the Patent Cooperation Treaty) Nov. 27, 2008.

* cited by examiner

PEDICLE BASED SPINAL STABILIZATION WITH ADJACENT VERTEBRAL BODY SUPPORT

CLAIM OF PRIORITY UNDER 35 U.S.C. §119

This application claims priority to U.S. Provisional Patent Application Ser. No. 60/865,359, titled Pedicle Based Spinal Stabilization with Adjacent Vertebral Body Support, file Nov. 10, 2006, and incorporated herein by reference as if set out in full.

CLAIM OF PRIORITY UNDER 35 U.S.C. §120

None.

REFERENCE TO CO-PENDING APPLICATIONS FOR PATENT

The present application is related to the following application, each of which is incorporated herein by reference as if set out in full:

U.S. patent application Ser. No. 10/915,902, title Screw and Rod Fixation System, filed Aug. 10, 2004;

U.S. patent application Ser. No. 11/128,962, titled Pedicle Screw Based Vertebral Body Stabilization Apparatus, filed May 12, 2005;

U.S. patent application Ser. No. 11/383,326, titled Pedicle Screw Based Vertebral Body Stabilization Apparatus, filed May 15, 2006; and U.S. patent application Ser. No. 11/420,417, titled Plate with Stabilization, filed May 25, 2006, which claims priority to U.S. Provisional Patent Application Ser. No. 60/711,352, filed Aug. 25, 2005; and

BACKGROUND

1. Field

The technology of the present, application relates to spinal corrective surgery and, more particularly to spinal fixation rods coupled to vertebral bodies having adjacent disc support extension.

2. Background

Back pain may be caused by degeneration or other deformities of an intervertebral disc ("diseased disc"). Conventionally, surgeons treat diseased discs by surgically removing the diseased disc and inserting an implant in the space vacated by the diseased disc, which implant may be bone or other biocompatible implants. The adjacent vertebrae are then immobilized relative to one another. Eventually, the adjacent vertebrae grow into one solid piece of bone.

Several techniques and systems have been developed for correcting and stabilizing the spine and facilitating fusion at various levels of the spine. In one type of system, a rod is disposed longitudinally along the length of the spine in the region of concern. The rod is arranged according to the anatomy and the correction desired. In this system, the rod is aligned along the spine and engages various vertebrae along its length. The rod engages, or more typically the parallel rods engage, the spine using fixation elements, such as, anchors attached to vertebral bodies by a bone screw.

Non-fusion options for surgically removing pain generators recently have become more prevalent. Some non-fusion technologies include distracting the intervertebral disc spate while allowing some motion. Generally, the non-fusion options have extension stops to limit the compression of the disc space, but attempt to provide more freedom of motion in flexion. Refer to the above incorporated applications U.S. patent application Ser. No. 11/128,962, titled Pedicle Screw Based Vertebral Body Stabilization Apparatus, filed May 12, 2005, and U.S. patent application Ser. No. 11/383,326, titled Pedicle Screw Based Vertebral Body Stabilization Apparatus, filed May 15, 2006, for more information on non-fusion pedicle based systems.

Limiting the range of motion of a spinal segment, whether immobilizing the segment (fusion) or limiting the motion of the segment (non-fusion) can place additional stress on adjacent or proximate vertebral segment. This additional stress may accelerate or contribute to the degeneration of adjacent discs or the like. Sometimes adjacent or proximate segments may already have some degeneration or other deformity that is exasperated by the limited motion of the adjacent or proximate segment.

Thus, against this background, it would be desirous to develop a technology that provides some support for adjacent or proximate spinal segments to inhibit any or additional degeneration.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout.

DETAILED DESCRIPTION

The word "exemplary" is used herein to mean "serving as an example, instance, or illustration." Any embodiment described herein should be construed as "exemplary," unless explicitly stated otherwise, whether it is specifically referred to as exemplary or not, and is not necessarily to be construed as preferred or advantageous over other embodiments.

The technology of the present application will now be described with specific reference to the figures. While the figures specifically refer to fusion devices, one of ordinary skill in the art will recognize on reading the disclosure that the technology of the present application could similarly be used on non-fusion devices.

Figure 1:
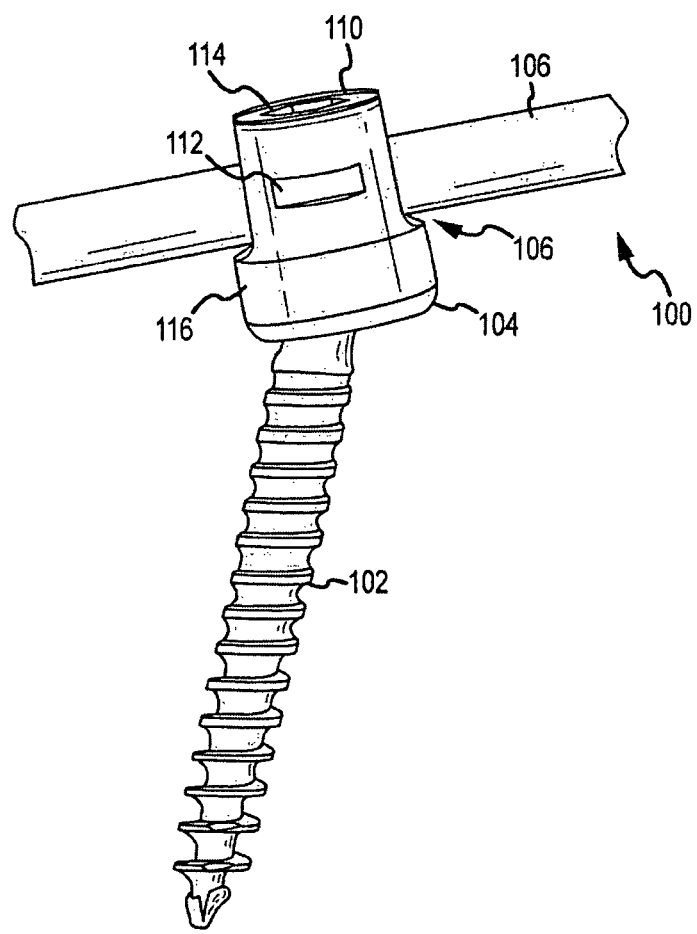
FIG. 1 is perspective view of a screw and rod fixation system consistent with the technology of the present application.
Figure 2:
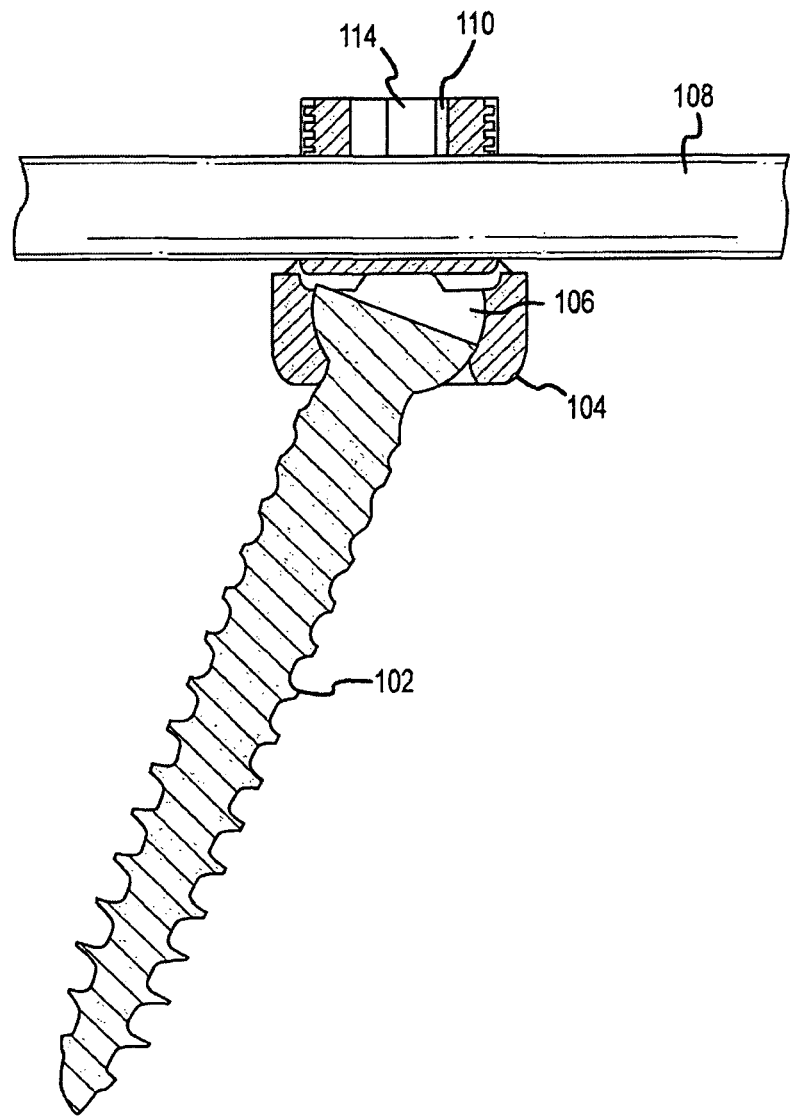
FIG. 2 is a cross sectional view of FIG. 1.

Referring now to FIG. 1 and FIG. 2, and in accordance with certain embodiments of the present invention, a screw and rod fixation system 100 is shown. FIG. 1 shows a perspective view of system 100 while FIG. 2 shows a cross-sectional view of system 100. System 100 includes a bone screw 102, a housing 104 having a sidewall insert 106, a rod 108, and a compressive member, such as, a setscrew 110. While rod 108 is shown extending completely through housing 104, rod 108 may only traverse partially through housing 104 and terminate. Bone screw 102, housing 104, or some combination thereof may contain one or more first mating surfaces 112. First mating surfaces 112 are designed to mate with a tool (not specifically shown). Also, setscrew 110 typically has one or more second mating surface 114 to mate with a tool (also not shown). As shown in FIG. 1, first mating surfaces 112 are actually slots on an outer surface 106 of housing 104. While shown as slots, first mating surfaces 112 may be any number of designs including one or more dimples, hex detents, or other equivalent mechanisms as are known in the art. Second mating surface 114 is shown with a hex shape to accept as hex driver useful in threading the setscrew. Of course, one of ordinary skill in the art would recognize other and equivalent first and second mating surfaces 112, 114 are possible.

Figure 3:
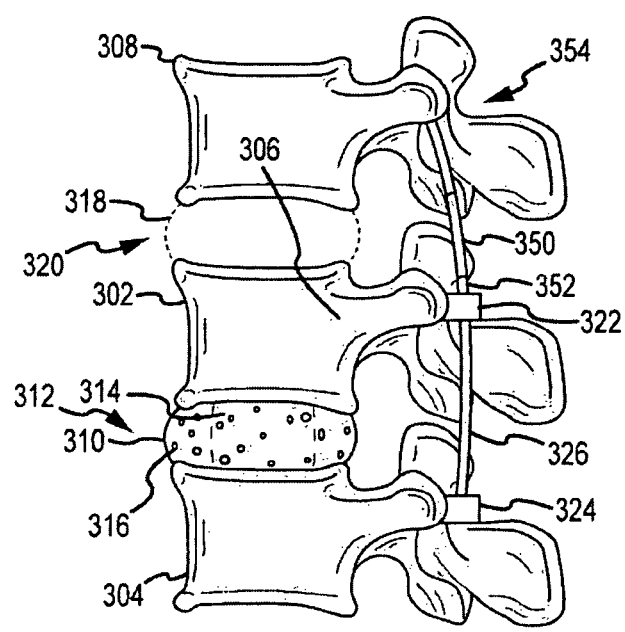
FIG. 3 is a lateral view of a screw and rod fixation system with adjacent disc and vertebral body support consistent with the technology of the present application.

Referring now to FIG. 3, a lateral view of spinal segment 300 is shown slightly exploded for convenience. Spinal segment 300 includes, for example, a superior vertebral body 302 and an inferior vertebral body 304 that are separated by an intervertebral disc 310 in intervertebral disc space 312. In some instances, a fusion implant 314 and/or biologics 316 may reside in disc space 310 as well to promote fusion. FIG. 3 further shows an adjacent or proximate vertebral body 308 superior to superior vertebral body 302. Proximate vertebral body 308 is separated from superior vertebral body 302 by an adjacent disc 318 in adjacent disc space 320. While shown proximate superior vertebral body 302, one of ordinary skill in the art would now understand the proximate vertebral body 308 could be proximate inferior vertebral body 304.

A superior pedicle screw 322 is fastened to superior vertebral body 302 and an inferior pedicle screw 324 is coupled to inferior vertebral body. A member 326, conventionally a rod, extends between superior pedicle screw 322 and inferior pedicle screw 324. For fusion, member 326 may be a substantially ridged. For non-fusion, member 326 may be relatively flexible or contain a motion dampening portion.

Figure 4:
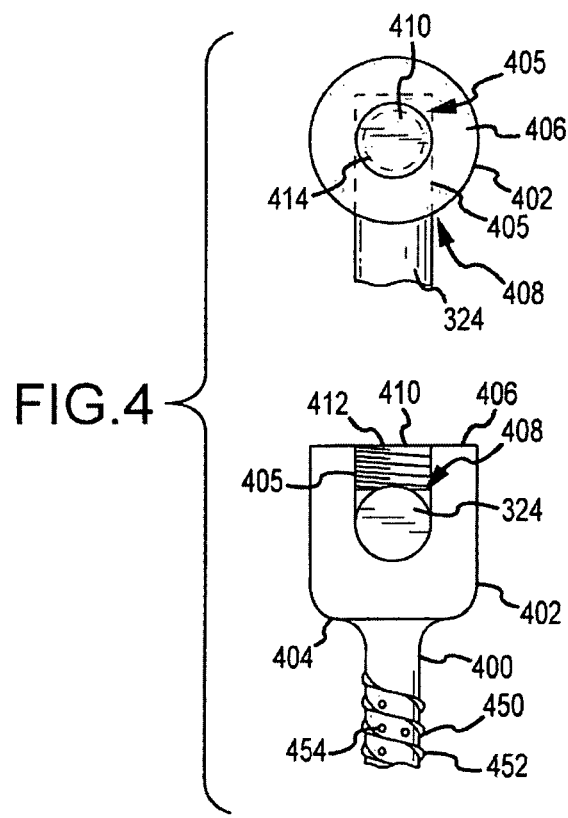
FIG. 4 is a pedicle screw and anchor consistent with the technology of the present application.

FIG. 4 shows a top and side view of a pedicle screw and anchor that could be used as pedicle screw 322 and 324. As shown in FIG. 4, a pedicle screw 400 and anchor 402 are provided to which member 326 may be attached. Anchor 402 has a bone engaging surface 404 and a top 406 opposite the bone engaging 404. A bore 405 extends from the top 406 to the bone engaging surface 404. A channel 408 extends from the top 406 towards bone engaging surface 404. Channel 408 is designed to fit member 326. Channel 408 may be open on two sides of anchor 402, similar to a spinal rod system, or open on a single side of anchor 402 (as show). A setscrew 410 having first threads 412 to thread onto corresponding threads 414 in bore 405 to couple member 326 to pedicle screw 400 and anchor 402. To facilitate the pedicle screws being permanently threaded into pedicles, thread 450 may be coated with bone growth materials 452, as those materials are conventionally understood in the art. Moreover, the pedicle screws may include bone growth channels 454 to promote bone growth through the pedicle screws. Channels 454 may be coated and/or packed with bone growth material. As one of skill in the art would now recognize, the pedicle screws may be similar to bone growth or fusion cages.

Referring back to FIG. 3, an adjacent disc support 350 is shown extending from superior pedicle screw 322 towards proximate vertebral body 308. Adjacent disc support 350 may be coupled to superior pedicle screw 320 using, for example, anchor 402 as shown in FIG. 4. Alternatively, and as shown, adjacent disc support 350 may be connected to pedicle screw 322 (or anchor 402) using a connection 352.

Adjacent disc support 350 may be a flexible member, shaped similar to a rod, such as, for example, biocompatible spring metals, elastic shaped memory alloys, composites, polymers, or the like. Adjacent disc support 350 extends to a location 354 proximate or abutting aportion of proximate vertebral body 308. For example, adjacent disc support may connect to the lamina, the pedicle, the facet, the spinous process or the like of proximate vertebral body 308. When adjacent disc support 350 comprises a flexible material, connection 352 of adjacent disc support to anchor 402 or pedicle screw 322 does not need to be a pivotal connection as the flexibility of the member may allow a sufficient range of motion. However, when adjacent disc support 350 is not a flexible member, connection 352 should be a pivotal or rotationally enabled connection, such as, for example, if the connection comprises shaped memory alloys, elastic biocompatible polymers or synthetics, elastic biocompatible metals, a hinge connection, a ball and socket joint, other modular connections, or the like.

Figure 5:
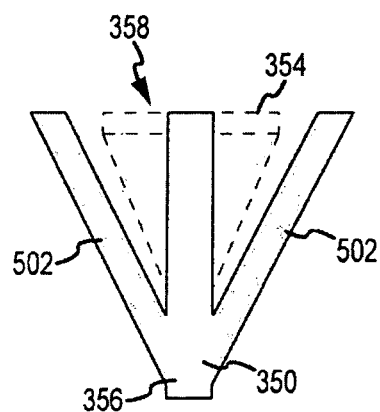
FIG. 5 is an elevation view of an adjacent disc and vertebral body support consistent with the technology of the present application.

Adjacent disc support 350 is shown extending about the pedicle section of adjacent disc 314. However, adjacent disc support 350 may reside about alternative sections of proximate vertebral body 308, such as, for example, about the facet, the spinous process, the lamina, or the like as a matter of design choice, surgical preference, anatomy, a combination thereof, or the like. Moreover, as shown in FIG. 5, adjacent disc support 350 may flare 358 at its distal end 354 or along its length from proximal end 356 to distal end 354 as shown in phantom. The flaring portion 358 may be a constant diverging portion, a random flaring portion, a T-shape, or the like. Flaring portion 358 also may be shaped to conform to biological anatomy. Moreover, referring to FIG. 5, distal end 354 of adjacent disc support 350 may include multiple prongs 502 to abut different portions of the adjacent disc. While shown as having three prongs, prongs 502 may be two, three, or more prongs.

Figure 6:
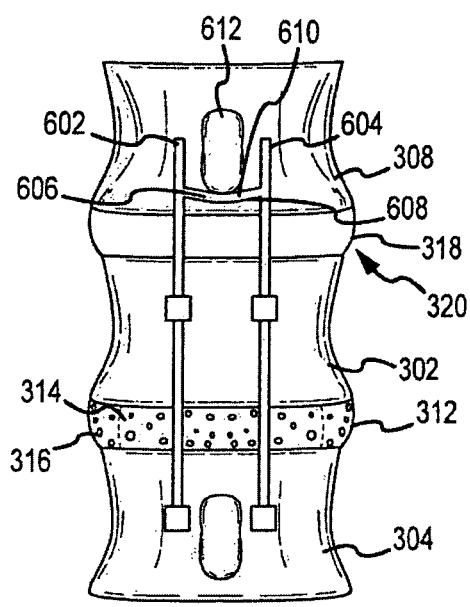
FIG. 6-11 are additional elevation views of adjacent disc and vertebral body supports consistent with the technologies of the present application.

Referring now to FIG. 6, a posterior view of segment 300 is shown. Similar to FIG. 3 above, segment 300 includes, for example, a superior vertebral body 302 and an inferior vertebral body 304 that are separated by an intervertebral disc space 312 having implant 314 and/or biologics 316 to promote fusion. Segment 300 further provides adjacent or proximate vertebral body 308 superior to superior vertebral body 302. In this case, the spinous process associated with superior vertebral body 302 has been removed as part of the fusion process. Proximate vertebral body 308 is separated from superior vertebral body 302 by an adjacent disc 318 in adjacent disc space 320. While shown proximate superior vertebral body 302, one of ordinary skill in the art would now understand the adjacent vertebral body could be proximate inferior vertebral body 304.

As can be seen, the technology described above may be implanted on both sides of the vertebral body by providing adjacent disc supports 602 and 604. In this case, adjacent disc support 602 may have a coupling extension 606 and adjacent disc support 604 may have a coupling extension 608 forming a support 610 for adjacent body spinous process 612. As the support is connected the vertebral body 302, support 610 maintains a constant distance and extension support for adjacent intervertebral disc, in other words an extension stop.

Using the above described process, adjacent disc support 350 could be arranged to extend from L5 to S1 to provide support. In this case, a bone fastener would be attached to L5 and the adjacent disc support would extend from the bone fastener to S1 that may have a bone fastener for a flexible connection. Alternatively, adjacent disc support 350 may abut S1 to provide an extension stop device without the anchor.

Figure 7:
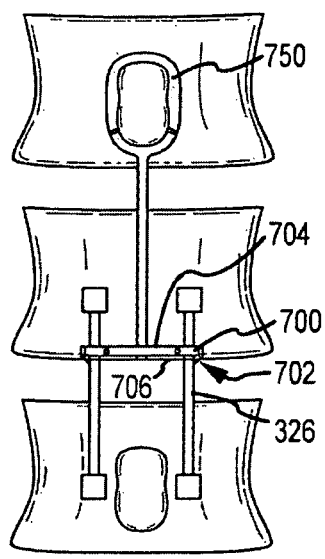

Instead of anchoring adjacent disc support 350 to a bone fastener, which would typically be a pedicle screw and anchor, it may be possible to connect adjacent disc support 350 to a cross bar 700 extending between members 326, as shown in FIG. 7. Cross bar 700 may be connected to members 326 using any conventional means, but, it is envisioned such a connection will include a hook part 702 hooking around the outside of the elongated members 326 and a setscrew 704 or other compression member threaded through bore 706 on cross bar 700. Cross bar 700 may be affixed length L or a variable length, for example, see U.S. patent application Ser. No. 11/217,787, titled "Spinal Rod Cross-Connect," incorporated herein by reference as if set out in full. Cross bar 700 would be especially useful in procedures where the spinous process is removed, as shown in FIG. 7.

As shown in FIG. 7, but usable with any embodiment of the present invention, a flexion stop device 750 can be coupled to adjacent disc support 350. In this case, the extension stop and the flexion stop are incorporated into a single band of material wrapped completely or partially about the spinous process, such as, for example, a cerclage bands, metal bands, sutures, or the like. Extension stop and flexion stop may be a single integrated material or multiple parts connected together as a matter of design choice. Moreover, the devices could be elastic materials to provide dampened movement, such as would be possible using shaped memory alloys, spring metals, polymers, resins, composites, and the like. Flexion stop device 750 may comprise a loop of material such as a suture or wire attached to adjacent disc support 350 or some other portion of the construct.

Referring now to FIGS. 8-11, additional examples of constructions for the proximate vertebral body support are provided. Again, for the additional examples, the proximate vertebral body 308 is shown as adjacent the superior vertebral body, but could be adjacent the inferior vertebral body. Moreover, the adjacent support could extend to on both the superior and inferior sides in certain conditions.

Figure 8:
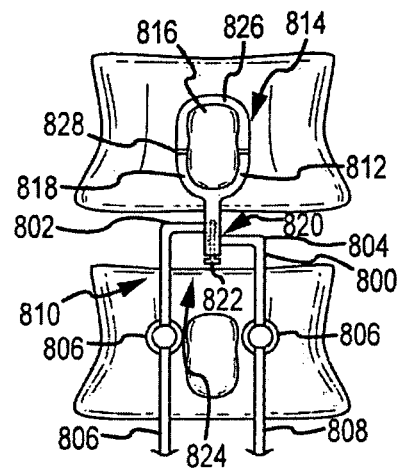

FIG. 8 shows a cross brace 800. Cross brace 800 has a first arm 802 and a second arm 804 extending laterally across the spine. First arm 802 and second arm 804 are coupled to superior pedicle screw anchors 806. First arm 802 and second arm 804 may be separate pieces or integrated with rod 808 such that rod 808 has a longitudinally extending portion 810 and laterally extending portion, a.k.a. first arm 802 and/or second arm 804.

A saddle 812, which may be U shaped as shown, provides a channel 814 in which adjacent spinous process 816 rests. Saddle 812 has a base 818 having a connection 820 for first arm 802 and second arm 804. The connection 820 may be a lateral bore through which arms 802 and 804 extend. A set screw 822 may extend through a connection bore 824 to connect saddle 812, first arm 802, and second arm 804. A band 826 may couple to the ends 828 of saddle 812 and wrap around adjacent spinous process 814 to provide a flexion stop.

Figure 9:
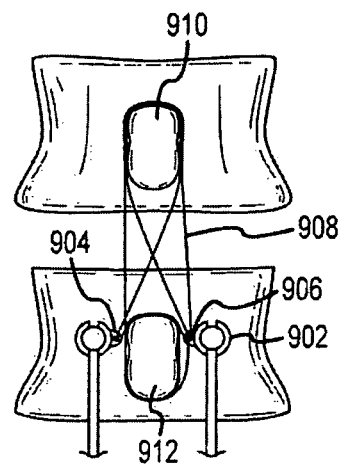

Referring now to FIG. 9, anchors 902 are shown having laterally extending tabs 904 with eyelets or through holes 906 in tabs 904. Bands 908 can be laced around adjacent spinous process 910 (and superior/inferior spinous process 912 if available) to provide both a flexion and extension stop. Bands 908 may be provided by cerclage bands, sutures, cables, wires, or the like.

Figure 10:
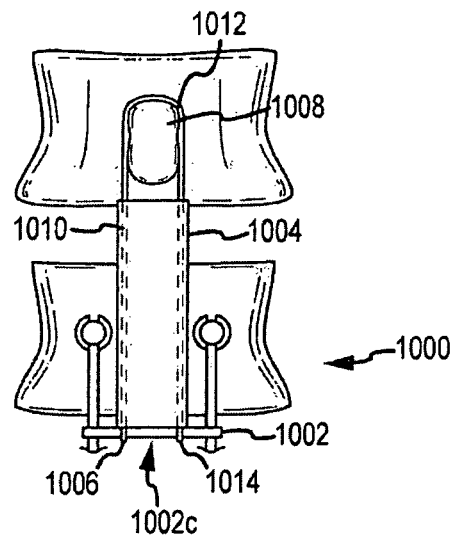

Referring now to FIG. 10, a conventional pedicle screw and fixation system 1000 is provided with a cross link 1002. Cross link 1002 may be a specially designed cross link with a flat center portion 1002c to support a spacer 1004. Alternatively, cross link 1002 may be a conventional cross link to which spacer 1004 is connected. to cross link 1002 by a connector 1006. Spacer 1004 may be relatively blunt to allow adjacent spinous process 1008 to rest on spacer 1004 or it may form a saddle similar to saddle 812 above. Spacer 1004 includes one or more through holes 1010 (shown in phantom). Connector 1006 comprises a band 1012 attached to cross link 1002 by a loop or a tie 1014. Band 1012 extends from cross link 1002 through through holes 1010, around adjacent spinous process 1008, back through through hole 1010, and is lopped or tied 1014 to cross link 1002. Thus, band 1012 provides a flexion stop or limit while spacer 1004 provides an extension stop. If a flexion stop or limit is not desirous, connector 1006 does not need to loop adjacent spinous process 1008.

Figure 11:
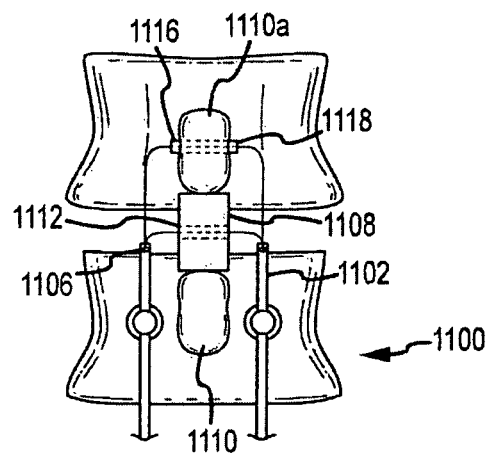

Referring now to FIG. 11, a conventional pedicle screw and fixation system 1100 is provided. Tabs 1102 are shown extending toward the proximate vertebral body from superior pedicle screw 1104. Tabs may be rod extensions as shown or separate protrusions with eyelets 1106. Optionally, a spacer 1108 resides between two spinous process 1110. Spacer 1108 has a through hole 1112 shown in phantom. Bands 1114, such as sutures, cables, wires, cerclage bands, or the like are laced between eyelets 1106 through spacer 1108 or about adjacent spinous process $1110_a$ to provide a flexion limit or stop. and extension stops by coupling the bands to eyelets 1106 and through through hole 1112. Optionally, load spreading unit 1116 having a through hole 1118 may reside at the end of spinous process $1110_a$ or be driven through the bone of spinous process $1110_a$ as shown. Spacer 1108 and load spreading unit 1116 may be bone, PEEK, metals, alloys, or the like as a matter of design choice. Bands 1114 may be wrapped about the one, both, or more spinous process as a matter of design, anatomy, and surgical preference.

The previous description of the disclosed embodiment is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

I claim:

1. A fusion device comprising a plurality of fasteners adapted to couple a plurality of housings to vertebral bodies and a plurality of rods coupled to the housings and adapted to extend longitudinally between vertebral bodies to promote fusion between the vertebral bodies, the fusion device further comprising at least one cross-link between the plurality of rods, the improvement comprising:
   an extension coupled to the cross-link, the extension adapted to traverse an adjacent intervertebral disc space and reside proximate an adjacent vertebra in selective abutment with the adjacent vertebra, such that the extension provides an extension stop to resist movement of the adjacent vertebra in extension while allowing movement of the adjacent vertebra in flexion such that bone fusion across the adjacent intervertebral disc is inhibited; and
   a flexible band connected to the cross-link and adapted to connect the extension to the adjacent vertebra;
   wherein at least one through hole extends through the extension and the flexible band extends from the cross-link through the at least one through hole.

2. The fusion device in accordance with claim 1, where the extension comprises a blunt end proximate the adjacent vertebra and configured to allow an adjacent spinous process to selectively rest on the blunt end.

3. The fusion device in accordance with claim 1, where the extension comprises a saddle proximate the adjacent vertebra and configured to allow an adjacent spinous process to selectively rest in the saddle.

4. The fusion device in accordance with claim 1, wherein the flexible band is connected to the cross-link via a loop.

5. The fusion device in accordance with claim 1, wherein the flexible band is connected to the cross-link via a tie.

6. A fusion device comprising a plurality of fasteners adapted to couple a plurality of housings to vertebral bodies and a plurality of rods coupled to the housings and adapted to extend longitudinally between vertebral bodies to promote fusion between the vertebral bodies, the fusion device further comprising at least one cross-link between the plurality of rods, the improvement comprising:

an extension coupled to the cross-link, the extension adapted to traverse an adjacent intervertebral disc space and reside proximate an adjacent vertebra in selective abutment with the adjacent vertebra, such that the extension provides an extension stop to resist movement of the adjacent vertebra in extension while allowing movement of the adjacent vertebra in flexion such that bone fusion across the adjacent intervertebral disc is inhibited; and a flexible band connected to the cross-link and adapted to connect the extension to the adjacent vertebra;

wherein at least two through holes extend through the extension and the flexible band extends from the cross-link through a first of the at least two through holes, forms a loop adapted to wrap about an adjacent spinous process, and extends through a second of the at least two through holes to the cross-link.

7. The fusion device in accordance with claim 6, where the extension comprises a blunt end proximate the adjacent vertebra and configured to allow an adjacent spinous process to selectively rest on the blunt end.

8. The fusion device in accordance with claim 6, where the extension comprises a saddle proximate the adjacent vertebra and configured to allow an adjacent spinous process to selectively rest in the saddle.

9. The fusion device in accordance with claim 6, wherein the flexible band is connected to the cross-link via a loop.

10. The fusion device in accordance with claim 6, wherein the flexible band is connected to the cross-link via a tie.

* * * * *